(12) United States Patent
Kominis et al.

(10) Patent No.: US 10,867,173 B1
(45) Date of Patent: Dec. 15, 2020

(54) SYSTEM AND METHOD FOR BIOMETRICS IDENTIFICATION AND PUPILLOMETRY

(71) Applicant: QUANTUM BIOMETRONICS PRIVATE COMPANY, Heraklion Crete (GR)

(72) Inventors: Iannis Kominis, Heraklion (GR); Antonis Margaritakis, Chania (GR); Kostas Mouloudakis, Heraklion (GR); Georgia Anyfantaki, Rethymno (GR); Aikaterini Gratsea, Heraklion Crete (GR)

(73) Assignee: QUANTUM BIOMETRONICS PRIVATE COMPANY, Heraklion Crete (GR)

( * ) Notice: Subject to any disclaimer, the term of this patent is extended or adjusted under 35 U.S.C. 154(b) by 0 days.

(21) Appl. No.: 16/916,160

(22) Filed: Jun. 30, 2020

(30) Foreign Application Priority Data

Jul. 1, 2019 (GR) .............................. 20190100283

(51) Int. Cl.
*G06K 9/20* (2006.01)
*G06K 9/00* (2006.01)

(52) U.S. Cl.
CPC ....... *G06K 9/00604* (2013.01); *G06K 9/2027* (2013.01); *G06K 9/2036* (2013.01)

(58) Field of Classification Search
CPC ........... G06K 9/00604; G06K 9/00597; G06K 9/2027; G06K 9/2036
USPC ....................................................... 351/206
See application file for complete search history.

(56) References Cited

U.S. PATENT DOCUMENTS

| | | | |
|---|---|---|---|
| 8,092,021 B1* | 1/2012 | Northcott | A61B 3/1015 351/206 |
| 8,170,293 B2* | 5/2012 | Tosa | G06T 7/168 382/117 |
| 8,391,567 B2* | 3/2013 | Friedman | H04N 7/18 382/117 |
| 8,644,562 B2* | 2/2014 | Tosa | G06T 7/149 382/117 |
| 10,042,994 B2* | 8/2018 | Perna | G06K 9/00604 |
| 10,425,814 B2* | 9/2019 | Perna | H04W 12/0605 |
| 10,643,087 B2* | 5/2020 | Green | G06K 9/0061 |
| 2005/0249377 A1* | 11/2005 | Fouquet | G01J 3/10 382/103 |

(Continued)

*Primary Examiner* — William R Alexander
(74) *Attorney, Agent, or Firm* — Patshegen IP LLC; Moshe Pinchas

(57) ABSTRACT

A system for photonic illumination for biometric identification and pupillometry. The system includes at least one light source configured for illuminating coherent beam including spatial superposition of at least a first wavelength and a second wavelength, the first wavelength is in the visible spectrum and the second wavelength is in the infrared spectrum. The system further includes an LCD dot array disposed along optical path of the beam such that the beam provides a spatially selective illumination having a cross section including an array of discrete pixels and an optical system for illuminating a human eye with the spatially selective illumination and for reflecting infrared light in the spatially selective illumination towards a camera disposed along an optical axis such that an image obtained by the camera is superimposed of the illuminated eye and the infrared light reflected by the optical system.

17 Claims, 4 Drawing Sheets

(56) References Cited

U.S. PATENT DOCUMENTS

| | | | | |
|---|---|---|---|---|
| 2008/0044063 | A1* | 2/2008 | Friedman | A61B 3/14 |
| | | | | 382/117 |
| 2008/0152198 | A1* | 6/2008 | Tsukahara | G06K 9/00604 |
| | | | | 382/117 |
| 2010/0128221 | A1* | 5/2010 | Muller | G02B 21/0048 |
| | | | | 351/207 |
| 2013/0141560 | A1* | 6/2013 | Friedman | H04N 7/18 |
| | | | | 348/78 |
| 2015/0042951 | A1* | 2/2015 | Stanga | A61B 3/102 |
| | | | | 351/206 |
| 2017/0091548 | A1* | 3/2017 | Agrawal | G06K 9/209 |
| 2018/0279937 | A1* | 10/2018 | Medberry | A61B 5/4064 |
| 2018/0279948 | A1* | 10/2018 | Medberry | A61B 5/4064 |
| 2019/0332764 | A1* | 10/2019 | Jeon | G06F 21/45 |

* cited by examiner

Fig. (2A)
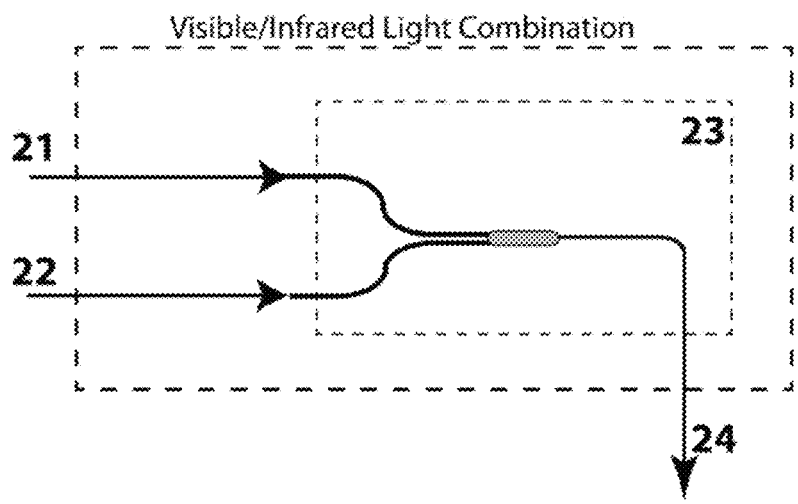
Fig. (2B)
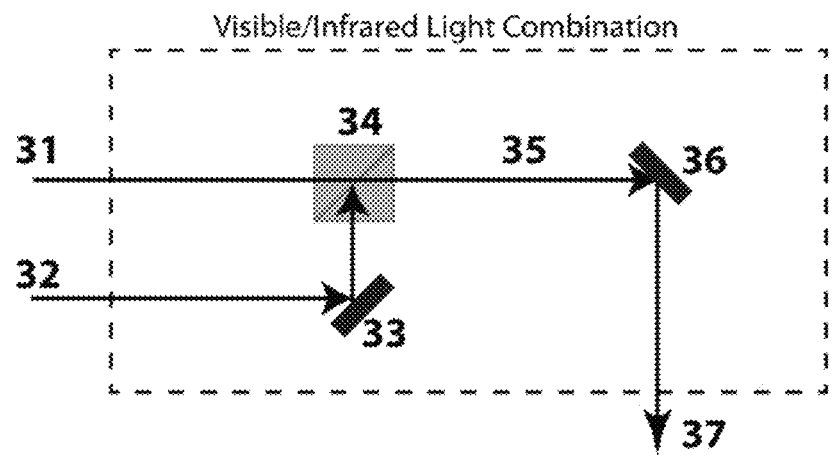
Fig. (2C)
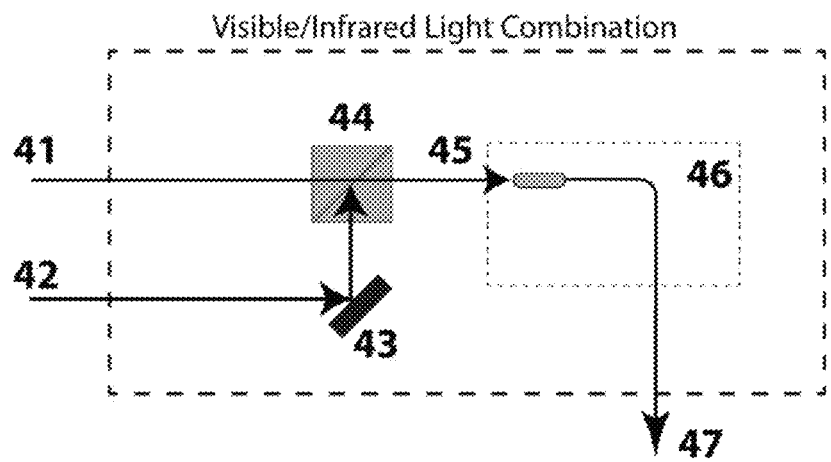

Fig. (4A)
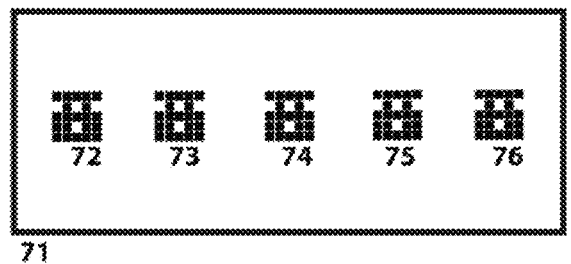
Fig. (4B)
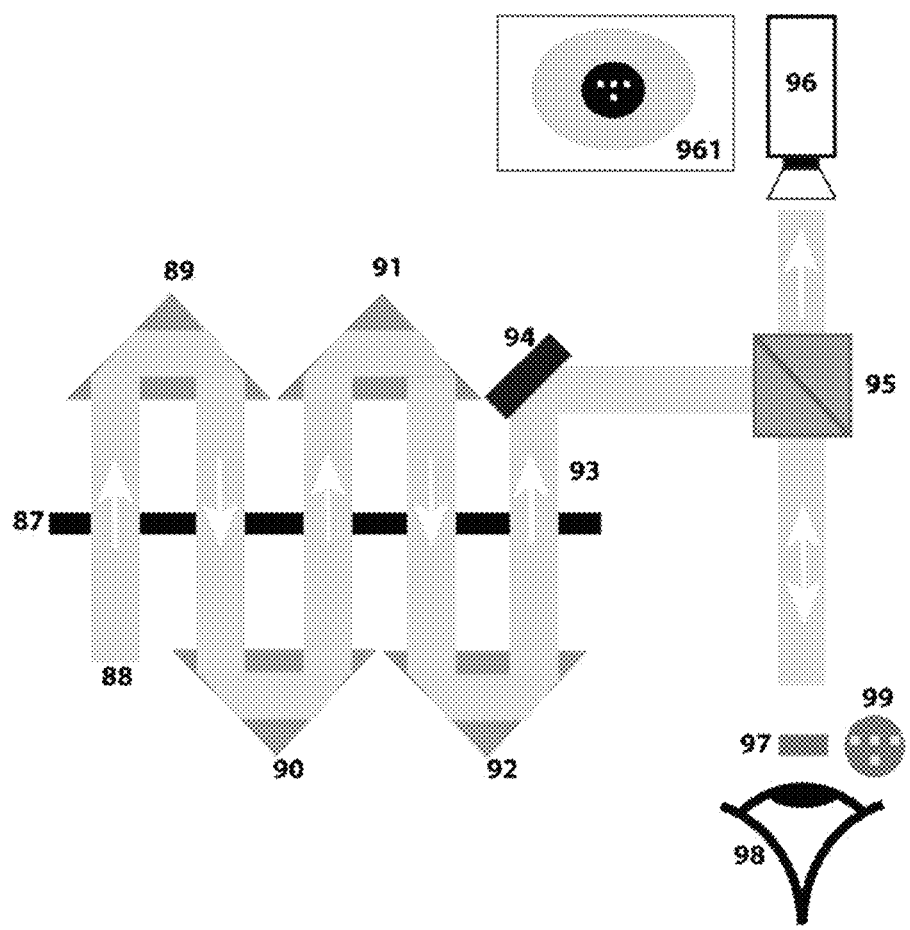

SYSTEM AND METHOD FOR BIOMETRICS IDENTIFICATION AND PUPILLOMETRY

FIELD OF INVENTION

The presently disclosed subject matter relates to a system and a method for photonic illumination in general, and in particular to photonic illumination for biometric identification and pupillometry.

BACKGROUND ART

References considered to be relevant as background to the presently disclosed subject matter are listed below:
(1) J. A. Unar, W. C. Seng and A. Abbasi, A review of biometric technology along with trends and prospects, Patt. Recogn. 47, 2674 (2014).
(2) M. Loulakis, G. Blatsios, C. S. Vrettou and I. K. Kominis, Quantum biometrics with retinal photon counting, Physical Review Applied 8, 044012 (2017).
(3) S. Mathot, Pupillometry: psychology, pshysiology and function, J. Cogn. 1, 1 (2018).
(4) A. Margaritakis, G. Anyfantaki, K. Mouloudakis, A. Gratsea and I. K. Kominis, Spatially-selective and quantum-statistics-limited light stimulus for retina biometrics and pupillometry, Applied Physics B 126, 99 (2020).

BACKGROUND

Current techniques for biometric identification, like iris scanning or face recognition, can in principle be foiled by a technologically sophisticated impostor, because they are based on classical information, like an image, which can be easily accessed and reproduced.

Copending U.S. patent application Ser. No. 16/500,101 discloses a biometric identification methodology, called quantum biometric identification, which is based on the perception of weak intensity light. In particular, this method relies on the measurement of the optical losses light suffers along its path from the cornea towards the retina. For a particular path, these losses are described by a parameter a, which can be measured if one knows the photon number incident on the user's eye, and using the user's perception or not of the light pulse containing this known photon number. The biometric id consists of an a-map of optical losses for a number of different paths of light from the cornea towards the retina. In contrast to existing methodologies, which in principle can be foiled, the quantum biometric methodology cannot be foiled. This is because the relevant "fingerprint" is encrypted in the eye, the retina and the brain, and because no matter what physical measurement an impostor impersonating an authentic user might perform on the light emitted by the biometric device's light source, as is the source described in the current invention, he/she cannot draw any conclusion about somebody else's (the authentic user's) "fingerprint".

In addition, current techniques for pupillometry, which is about the diagnostic measurement of the eye's pupil constriction/dilation under illumination, work with classical light emitting diode (LED) light sources, which indiscriminately illuminate the whole pupil with partially controllable light intensity.

SUMMARY OF INVENTION

There is provided in accordance with an aspect of the presently disclosed subject matter a system for photonic illumination for biometric identification and pupillometry. The system includes at least one light source configured for illuminating coherent beam including spatial superposition of at least a first wavelength and a second wavelength, the first wavelength is in the visible spectrum and the second wavelength is in the infrared spectrum. The system further includes an LCD dot array disposed along optical path of the beam such that the beam provides a spatially selective illumination having a cross section including an array of discrete pixels and an optical system for illuminating a human eye with the spatially selective illumination and for reflecting infrared light in the spatially selective illumination towards a camera disposed along an optical axis such that an image obtained by the camera is superimposed of the illuminated eye and the infrared light reflected by the optical system. The system further includes a controller for controlling illumination of the discrete pixels are and for controlling number of photons of the first wavelength per unit time per discrete pixel.

The at least one light source can include a first laser for illuminating a first laser beam in the visible spectrum and a second laser for illuminating a second laser beam in the infrared spectrum, and wherein the system further a wavelength combiner for superimposing the first and second beams into the coherent beam.

The wavelength combiner includes a first input fiber port for receiving the first beam and a second input fiber port for receiving the second beam, and an output fiber port for emitting the coherent beam, the wavelength combiner being configured such that the first and second wavelengths in the coherent beam are in the same spatial mode.

The wavelength combiner can include beam splitter having a first input port for receiving the first beam and a second input port for receiving the second beam, and an output port for emitting the coherent beam, the beam splitter includes an optical alignment configured such that the first and second beams are spatially superimposed including the first and second wavelengths.

The output port can include an optical fiber configured for propagation of the first and second wavelengths in the coherent beam are in the same spatial mode.

The system can further include a stabilizing device for stabilizing the intensity of the visible light against fluctuations in the intensity of the visible light.

The stabilizing device can include an acousto-optical crystal configured to receive and diffract light in the visible spectrum to any order other than the zero order.

The system can further include feedback circuit having an output configured to drive the acousto-optical crystal by a harmonic signal in the radiofrequency spectrum, such that the intensity directly depends on amplitude of the harmonic signal.

The system can further include a photodetector measuring the intensity of the visible light and wherein the feedback circuit includes an input formed as a difference of an output voltage of the photodetector and a reference voltage, the photodetector includes an optical filter configured for transmitting visible light and blocking infrared light such that intensity measured by the photodetector is only the intensity of the visible light.

The feedback circuit can include a voltage-controlled attenuator having an input of harmonic signal in the radiofrequency spectrum provided by a radiofrequency oscillator, the voltage-controlled attenuator being configured to provide an output signal having the frequency harmonic signal with an attenuated amplitude, wherein level of attenuation being controlled by a control voltage of the feedback circuit, and wherein the output signal is directed to a radiofrequency switch which drives a radiofrequency amplifier which drives the acousto-optical crystal.

The radiofrequency switch can cut off the radiofrequency harmonic signal from the acousto-optic crystal and as a result modulates in time the intensity of the visible light, with the result that laser pulses can be formed with a time duration controlled by the voltage of the voltage-controlled radiofrequency switch.

The system can further include a dichroic mirror configured to reflect majority of the visible light towards the photodetector and to transmit the entire infrared light, such that beam transmitted through the dichroic mirror contains visible and infrared light with intensities are at a ratio of 1:50.

The LCD dot array can include LCD geometric arrangements disposed along the optical path and being configured such the laser beam passes therethrough.

The optical path can include retroreflection prisms configured to allow passes of the laser beam through each one of the LCD geometric arrangements.

The optical system can include a beam splitter with an antireflective coating for infrared light, in such a way that it is the laser beam exiting the beam splitter that propagates towards the eye, and in such a way that a viewing camera sensitive to infrared light and positioned behind the beam splitter and focusing on the eye's pupil can record the eye's pupil, without the image being blurred by infrared light virtual reflections from the beam splitter, as a result of the antireflective coating for infrared light.

The system can further include a transparent glass positioned before the eye to be illuminated, in such a way that the infrared light of the laser beam is reflected backwards from the glass plate and is incident on the viewing camera after being transmitted though the beam splitter, in such a way that the viewing camera presents a superposition of the eye's pupil image with the arrangement of pixels of higher/lesser intensity, with the result that information can be registered on which particular points on the eye's pupil are being illuminated, with the further result that in subsequent measurements on the same human subject the same the spots can be systematically illuminated again.

The system can further include a set of converging and diverging lenses disposed with respect to the beam splitter in such a way as to collimate the diverging light beams reflected from the cornea and direct them into the viewing camera.

This invention is about the technological realization of a light source to be used as visual stimulus for the implementation of a new method of biometric identification of ultra-high security, and the advancement of pupillometry beyond the current state-of-the-art to a new realm of ultrahigh precision. In particular, the current invention describes the development of a coherent laser light source, the beam of which contains in perfect spatial overlap both visible radiation and infrared radiation, and the laser beam's cross section consists of discrete pixels, such that any pixel combination can be illuminated, as chosen by a computer. The photon number per illuminated pixel per unit time for the visible radiation is also computer controlled. Finally, the infrared light in the laser beam is not perceived by the human eye, but its reflection is visible by a camera, and thus information on which spots on the eye are illuminated by the laser beam's illuminated pixels is readily available.

For the sake of simplicity the following terms as used herein the specification and claims are defined as follows:

Coherent radiation is the radiation produced by a laser.

Photon is the quantum of electromagnetic radiation. Any light source of a given wavelength and given power emits a given photon number per unit time, on average. This means that measuring photon number during same time intervals, fluctuations about the given mean number will be observed. Among all classical light sources, these fluctuations are the smallest for coherent laser light of constant intensity, and they follow the Poisson distribution.

Light pulse is radiation, the electromagnetic field of which is nonzero only for a finite amount of time. In the current invention, when we refer to the phrase "per pulse", we mean that the light radiation is applied for a finite duration of time. For the quantum biometric methodology this duration is about 100 ms, while for the methodology of quantum pupillometry it usually is a few seconds.

Stimulus light is the visible light causing the human subject to have his/her visual system stimulated by illuminating some part of the retina.

BRIEF DESCRIPTION OF THE DRAWINGS

In order to understand the disclosure and to see how it may be carried out in practice, embodiments will now be described, by way of non-limiting examples only, with reference to the accompanying drawings, in which:

FIG. 2A is a block diagram illustration of a wavelength combiner in accordance with an example of the presently disclosed subject matter;

FIG. 2B is a block diagram illustration of a wavelength combiner in accordance with another example of the presently disclosed subject matter;

FIG. 2C is a block diagram illustration of a wavelength combiner in accordance with yet another example of the presently disclosed subject matter;

FIG. 4A is a pixel array including a plurality of LCD geometric arrangements in accordance with an example of the presently disclosed subject matter; and FIG. 4B, is a schematic illustration of the optical path of the combined beam in accordance with an example of the presently disclosed subject matter.

DETAILED DESCRIPTION OF EMBODIMENTS

Figure 1:
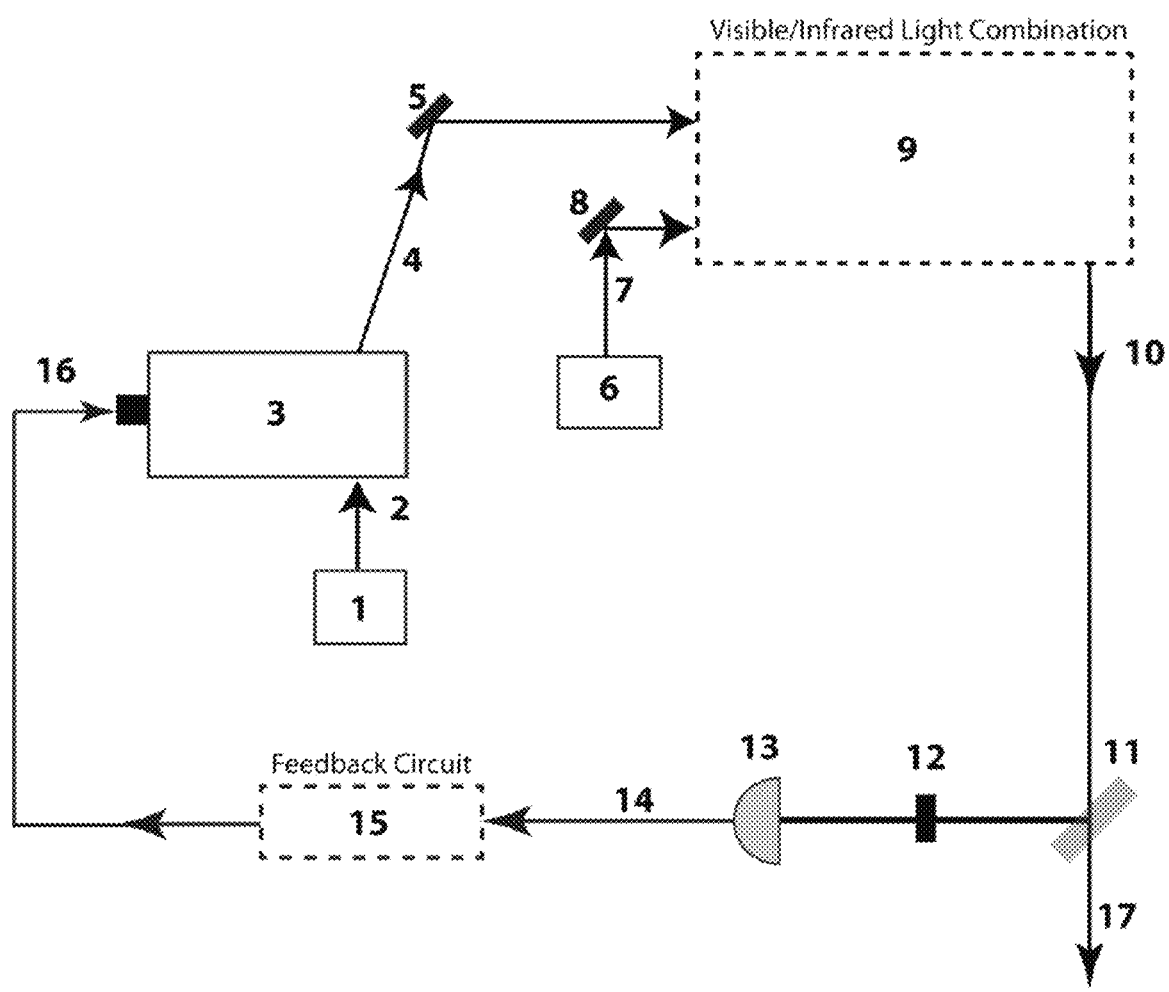
FIG. 1 is a block diagram illustration of an optoelectronic system in accordance with an example of the presently disclosed subject matter.

Copending U.S. patent application Ser. No. 16/500,101 discloses a biometric identification methodology, called quantum biometric identification, which is based on the perception of weak intensity light. In particular, this method relies on the measurement of the optical losses light suffers along its path from the cornea towards the retina.

For this methodology to be implemented, it is required to illuminate the eye's pupil on various spots, with light pulses of duration between 100-200 ms, and photon number between 20-200 photons. This number must be known with the maximum possible precision, and it must also be computer controlled. Moreover, which spot on the pupil is illuminated or which group of spots are illuminated simultaneously, must also be computer controlled. Both parameters, (a) photon number per pulse per illuminated pixel, and (b) geometrical arrangement of illuminated pixels should be computer controlled so that their variation is straightforward during the identification process without the need of human intervention. (c) Lastly, it is desired to acquire information on which particular spots on the eye are actually illuminated, so that in a future measurement the illumination of the same spots can be repeated.

The current invention is about the development of the photonic technology providing for a light source with the previous required characteristics (a)-(c). The same technology can be used in pupillometry.

Contrary to known biometric identification methods, which can be easily accessed and reproduced, biometric identification methods including the light source in accordance with the present invention remedy the problem, because they are based on the human visual system's ability to perform photon counting, and their security is derived from the laws of quantum physics of photodetection of coherent radiation, while the relevant biometric information is encrypted in the eyeball, the retina and the brain, and hence is not accessible.

Similarly, with regards to pupillometry, the current invention provides spatially selective illumination of specific spots on the pupil, and hence the spatially selective stimulation of specific spots on the retina, with laser light having precisely known intensity. The spatially selective pupil illumination and retina stimulation can lead to much larger quantities of neural information from the pupil diameter changes.

All pupillometers currently available in the market indiscriminately illuminate the whole eye with LED light, and do not provide the possibility for spatially selective illumination. The current invention can advance pupillometry to a higher level of precision and thus a higher level of accessible diagnostic information retrieved from the measurements of pupil's diameter, since the illuminating light is in the form of a laser beam, the cross section of which consists of discrete pixels, which can be independently illuminated or not, and moreover there is the ability to know which spot on the pupil was illuminated.

Thus, the photonic technology of the current invention can be used for two different purposes, for biometric identification of ultrahigh security, and for pupillometry with ultrahigh spatial resolution. Next, the optical and optoelectronic configuration realizing the aforementioned light source will be explained.

FIG. 1 shows a block diagram illustration of the optoelectronic system 100 which provides a laser light beam which contains visible and infrared light in spatial superposition with relative intensities at a predetermined level, and with the visible light intensity being (a) stabilized and (b) computer controlled by a computer providing a voltage reference, so that this intensity can be modified.

The optical setup is based on two lasers, one operating in the visible part of the spectrum at 532 nm, and the other in the infrared part of the spectrum at 850 nm. The exact wavelengths are not critical. The same technology can equally work for other choices of wavelengths in the visible and infrared part of the spectrum.

The first element of the invention is that the beams of the two lasers are combined in one beam containing both the visible and the infrared light.

As shown in FIG. 1, the optoelectronic system 100 includes a first laser source 1 which emits a first laser beam in the visible spectrum 2 and a second laser source 6 which emits a second laser beam in the infrared spectrum 7. The optoelectronic system 100 further includes mirrors 5 and 8 for directing the first and second laser beams 2 and 7, respectively, towards a wavelength combiner 9.

Combing the first and second laser beams 2 and 7 in the wavelength combiner 9, can be carried out in various manner, as shown in FIGS. 2A-2C. According to the Example shown in FIG. 2A, the wavelength combiner can be an optical fiber combiner of visible/infrared (Fiber wavelength combiner, Thorlabs NG71F1 or equivalent product), which includes two input fibers 21 and 22 (one for the visible light, and one for the infrared light), a wavelength combining device 23 and one output fiber 24, from which both input beams exit as one beam. Thus the two light wavelengths are spatially superimposed in the same spatial mode, and hence have the exact same propagation in space.

Alternatively, as shown in FIG. 2B, one can use a beam splitter 34, on a first input 31 of which the visible light is incident, and a second input 32 on which the infrared light is incident, which input is directed to the beam splitter 34 with a mirror 33, in such a way that in the output 35 of the beam splitter 34 both beams are present. A mirror 36 can utilized to direct the combined beams toward the output 37. This method requires precise optical alignment of the two beams. Given that the beam profile of the beams coming from different lasers is different, this method will lead to not a perfect spatial superposition of the two wavelengths.

According to another example, as shown in FIG. 2C, a beam splitter 44, such as shown in FIG. 2B, can be used for receiving beams of the first and second inputs 41 and 42, the second input 42 directed towards the beam splitter 44 with a mirror 43, but with the output beam 45 of the beam splitter 44 containing both wavelengths entering an optical fiber 46 supporting both wavelengths and providing in its output 47 a single beam containing both visible and infrared light.

According to either one of the examples of FIGS. 2A-2C, the output of the wavelength combiner provides a laser beam in which both visible and infrared light propagate together.

Referring back to FIG. 1, the optoelectronic system 100 further includes a intensity stabilization scheme of the intensity of the visible light from the first laser source 1, to be used when the visible/infrared light is combined according to the examples of FIGS. 2A and 2C, both of which include an optical fiber.

It is noted that the fiber causes random intensity fluctuations in the light exiting the fiber. For the infrared light these fluctuations are of no concern, but for the visible light they are disturbing, because it is required that the intensity of the visual light stimulus reaching the eye is stable and controllable. To stabilize the visible light intensity exiting the wavelength combiner 9 the visible light is first sent into an acousto-optical crystal 3, and the beam diffracted by the crystal is input to the wavelength combiner 9.

The combined beam 10 exiting the wavelength combiner 9 includes both visible and infrared light in a perfect spatial superposition. The combined beam 10 is directed towards a dichroic mirror 11 having a high transmissivity in the infrared spectrum and a high reflectivity in the visible spectrum. The function of the dichroic mirror 11 is explained hereinafter, and is configured such that a small part of the combined beam 10 is sampled and a first portion of the combined beam is directed to a photodetector 13 while a second portion of the combined beam 17 propagates towards the next stage of the setup, which is depicted in FIG. 4B.

The optoelectronic system 100 further includes an optical filter 12 blocking infrared light before the first portion of the combined beam reaches the photodetector 13.

Next, the output voltage 14 of the photodetector 13 is compared to a stable reference voltage. The difference of the two voltages is the input of a feedback circuit 15, the output of which is a harmonic signal in the radiofrequency spectrum which is coupled to and drives the acousto-optical crystal 3.

It is noted that since the intensity of the diffracted beam exiting the acouto-optic crystal is directly dependent on the amplitude of the harmonic radiofrequency signal (within the spectrum 50-500 MHz) driving the crystal, the feedback circuit 15 regulates exactly this amplitude, in a way that the fluctuations of the visible light intensity exiting the wavelength combiner 9 are cancelled.

Figure 3:
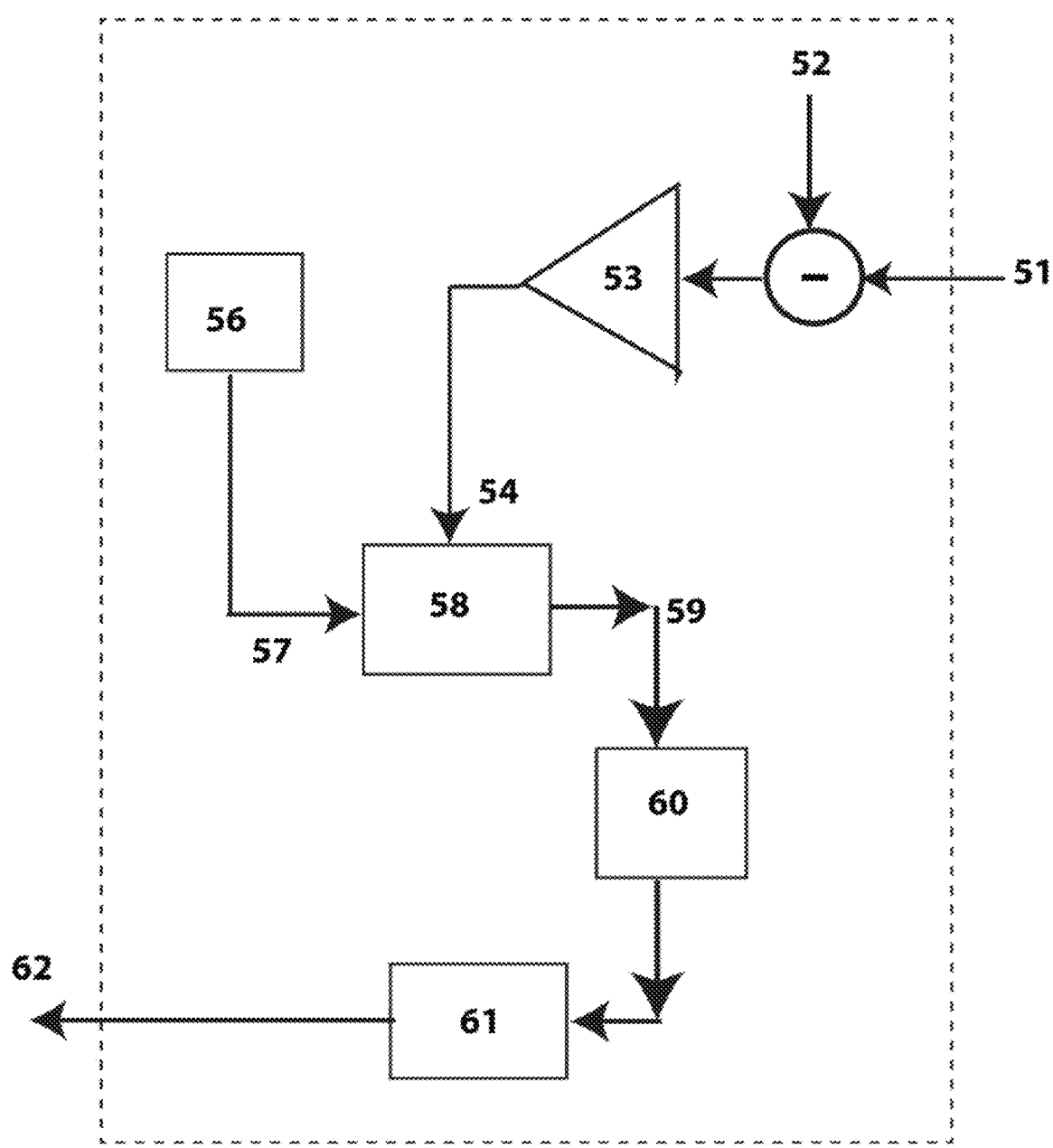
FIG. 3 is a block diagram illustration of feedback circuit in accordance with another example of the presently disclosed subject matter.

According to an example, as shown in FIG. 3, the opto-electronic feedback circuit 15 works as follows. The voltage resulting from the difference of the photodetector voltage 51 and the reference voltage 52 drives a proportional/integral feedback circuit 53, the output voltage 54 of which controls a voltage-controlled attenuator 58. The attenuator 58 takes as input a harmonic signal 57 in the radiofrequency spectrum provided by a radiofrequency oscillator 56, and is configured such that the output signal 59 has the same frequency harmonic signal 57 but with an attenuated amplitude, the level of attenuation being controlled by the control voltage 54.

The attenuator's output signal 59 goes to a radiofrequency switch 60, the output of which drives a radiofrequency amplifier 61, the amplifier output 62 is then directed to drive the acousto-optical crystal.

Thus, the visible light intensity in the beam diffracted by the crystal is regulated by the control voltage of the attenuator circuit, which is automatically regulated by the proportional/integral feedback circuit 15 in such a way as to cancel any fluctuations of the visible light intensity caused by the fiber combiner. In other words, the photodetector 13 voltage is actively locked to the reference voltage 52, and hence the intensity of the visible light exiting the fiber combiner 9 is stabilized. With the radiofrequency switch 60 one can pause the operation of the acousto-optic crystal 3 by switching off its driving radiofrequency signal, thus eliminating the visible light entering the fiber combiner 9. This way one can create the optical pulses which are used to deliver the visible stimulus light only within well-defined time intervals.

According to an example of the invention, the visible light intensity can be controlled with a computer. Since the visible light intensity is actively locked to the reference voltage, changing the reference voltage one can change the intensity of the visible light exiting the fiber combiner 9. The reference voltage can be provided by the analog output card connected to a computer or an equivalent electronic circuit controlled by a computer. Thus the light intensity of the visible stimulus light exiting the fiber combiner 9 can be changed by a computer.

As indicated hereinabove the combined beam 10 is directed towards a dichroic mirror 11, which samples the visible light exiting the fiber combiner 9 in order to illuminate the photodetector 13 which drives the whole intensity stabilization process described previously. The dichroic mirror 11 reflects a large fraction (98\%) of the incident visible light, and transmits almost all the infrared light. Before illuminating the photodetector 13 positioned at the reflected output of the dichroic mirror, the laser beam goes through an optical filter cutting the infrared light, so that the photodetector 13, on the output of which is based the whole feedback circuit 15, measures only the intensity of the visible light.

Thus 2\% of the visible and almost 100\% of the infrared light incident on the dichroic mirror 11 are transmitted. Assuming equal visible and infrared intensities incident on the dichroic mirror 11, the beam transmitted by the dichroic mirror, which is directed to the rest of the optical setup, has thus inbuilt a relative imbalance of the visible/infrared light at the level of 1:50. The reason this is done is explained hereinafter, and has to do with the relative intensities of the visible/infrared light in the final laser beam illuminating the eye, so that the incidence spot on the eye is visible by a camera through the reflection of the infrared light.

Summarizing the above, a laser light beam is obtained which contains visible and infrared light in a perfect spatial superposition with relative intensities at the level of 1:50 (due to the dichroic mirror), and with the visible light intensity being (a) stabilized and (b) computer controlled by a computer providing a voltage reference, so that this intensity can be changed at will.

The next stage of the invention is about the spatial selectivity of the light source, that is, the formation of a laser beam profile including discrete pixels. This can be accomplished by using a transmissive liquid crystal graphic display (LCD), which consists of low-transmission and high-transmission dots. The display can be programmed by a computer in such a way that one can determine which dots will be low-transmission and which will be high-transmission. Programming the display is not part of this invention. The low-transmission dots impart an optical loss into the laser beam, which is higher than the optical loss imparted by the high-transmission dots. Thus, the laser beam profile is shaped into pixels through the LCD dots.

Next, by using the low-transmission dots of the LCD one can introduce an optical loss in the second part of the laser beam 17 that has been received from dichroic mirror 11. Thus, if one chooses which dots of the LCD will be "low-transmission" and which will be "high-transmission," one can transfer the arrangement of those low/high transmission LCD dots into an arrangement of dark/illuminated pixels of the laser beam's cross section.

In the example displayed in FIG. 4A the LCD includes an array of dots, each dot of size 1 mm by 1 mm. The dot array 71 includes LCD geometric arrangements 72-76 of LCD 5×5 dots which are identical, such that every time the laser beam passes through one of the LCD geometric arrangements 72-76, the formed pixels in the laser beam's cross section (in this case 25) go through the same arrangements of LCD dots. As a result, the optical loss responsible for the formation of the pixels is multiplicative with the number of passes and enhances the contrast between dark and illuminated pixels. This is done because for one pass of the laser beam through the LCD, the introduced optical losses are not enough to create dark/illuminated pixels in the laser beam's cross section having an adequate contrast. It is appreciated that other arrangements with more or less pixels are equally possible. Alternatively, instead of a multipass beam geometry using a single LCD, one can use a single pass through multiple LCDs having the exact same arrangement of dots and positioned in series.

As shown in FIG. 4B, the optoelectronic system includes an optical path having an LCD dot array 87, such as the one shown in FIG. 4A, and retro-reflecting prisms 89-92. The retro-reflecting prisms 89-92 are configured in such a way that the laser beam 88 coming from the second part 17 of the dichroic mirror crosses the LCD dot arrangement on the dot array 87 many times, in order to enhance the contrast between dark and illuminated pixels. The prisms 89-92 reflect the laser beam also introducing a horizontal displacement, so that the beam can go through the next arrangement of dots in the liquid crystal display The prisms 89-92 are positioned and the computer driving the LCD is programmed in such a way that in each pass the laser beam goes through the exact same arrangement of LCD dots, so that the total optical loss is multiplied pass by pass.

Accordingly, if for one pass the optical loss is 70\%, for 5 passes the optical contrast achieved is 0.3^5=0.002, which is adequate for using the laser beam in the biometric identification scheme. This is because this scheme requires up to 200 photons per pulse per illuminated pixel, so if the visible light intensity is such that the illuminated pixels contain 200 photons per pulse, the dark pixels will contain 200*0.002=0.4 photons. This means that once every two times the dark pixels will contain just one photon, and the other one time no photon, when the illuminated pixels contain 200 photons. Such a contrast is considered adequate, and can be further increased by more passes through the LCD.

The last stage of the system obtains information on the illumination geometry on the pupil. It is required to know the illumination geometry on the eye's pupil, so that in a second, third or any subsequent measurement one can illuminate the exact same spots on the pupil, and thus stimulate the exact same spots on the retina.

Accordingly, the laser beam 93 exiting the pixel array 87 is led by a mirror 94 to a beam splitter 95. The beam splitter 95 is configured such that a portion of the combined laser beam is reflected towards the eye 98. In the back of the beam splitter 95 there is a camera 96 sensitive to the infrared light as well as to the visual light. Since the eye 98 has a spherical geometry, when it is illuminated by parallel laser beams the beams reflected by the cornea are deflected relative to the horizontal direction of the incident beam, and it is difficult to detect them. This can be done with a converging lens of large diameter, which will collect the diverging beams, which then can be recollimated with a diverging lens before the camera.

Alternatively, collecting the light beams reflected from the cornea can be carried out with a transparent glass plate 97.

The glass plate 97 is positioned exactly before the eye, so that the infrared light in the illuminated pixels is exactly reflected backwards by the glass, and directly propagates towards the camera 96 after being transmitted by the beam splitter 96. This way, the illuminated pixels of the laser beam illuminating the eye become visible.

Finally, the beam which reaches the glass plate 97 includes the illuminated pixels 99 which correspond to the high-transmission dots in the LCD geometric arrangements 72-76. The image 961 which is received by the camera 96 on the other hand, includes a superimposed image of the eye's pupil and the infrared light pixels reflected by the glass plate 97. As a result it is possible to register which particular spots on the pupil are being illuminated.

At this point, the usage of the dichroic mirror 11 can be explained. Since the original laser beam exiting the wavelength combiner 9 contains the visible and infrared light in approximately equal intensities, if the intensity of this laser beam is reduced to the level that the visible light contains 20-200 photons per illuminated pixel per pulse, the infrared light will have a similarly very low intensity. Since the glass plate 97 reflects just 4\% of the incident intensity, the reflected infrared intensity will not be enough to be detectable by the camera 96. On the other hand, if just the visible light intensity is independently reduced before entering the wavelength combiner 9, so that the visible light exiting the wavelength combiner 9 has 20-200 photons per illuminated pixel per pulse, there will not be enough light for the photodetector 13, and hence not a measurable voltage at the photodetector's output to run the feedback circuit 15. The dichroic mirror 11 solves both aforementioned problems.

In other words, the light used for stimulating the visual system is the visible light. The laser beam is shaped in pixels by the LCD, with each pixel being either dark or illuminated, so that the exact spots on the pupil which is stimulated can be detected and subsequent visual stimulations can be sent to the exact same spots. Hence, it is required to obtain an image of the eye and as well as indication regarding the spots being illuminated.

For that reason, the combined beam illuminating the eye is also partially reflected by the glass plate 97 before entering the eye. The glass plate 97 sends the reflected light to the camera which provides an image of the illuminated eye as well as an image of the illumination reflected by the glass plate 97. This way the image 961 includes information regarding the illumination in the eye and the LCD geometric arrangement which indicates the exact spot in the eye which are illuminated.

Since the visual light does not have enough intensity for the reflected beam to be visible in the camera, the infrared light is added to the beam. The infrared light does not trigger the visual system, so it is perceived by the eye, however at the same time its intensity is large enough that the portion of the light reflected by the glass plate is visible in the camera. Having the infrared light be completely overlapped in space with the visible light through the combiner, it can be determined which spots in the eye are illuminated with the visible light.

The beam splitter 95 can include antireflective coating for infrared light so that there are no false reflections of the infrared light into the camera 96 that would obscure the light reflected from the glass plate preceding the eye.

Those skilled in the art to which the presently disclosed subject matter pertains will readily appreciate that numerous changes, variations, and modifications can be made without departing from the scope of the invention, mutatis mutandis.

The invention claimed is:

1. A system for photonic illumination for biometric identification and pupillometry the system comprising:
    at least one light source configured for illuminating coherent beam including spatial superposition of at least a first wavelength and a second wavelength, said first wavelength is in the visible spectrum and said second wavelength is in the infrared spectrum;
    an LCD dot array disposed along optical path of said beam such that said beam provides a spatially selective illumination having a cross section including an array of discrete pixels;
    an optical system for illuminating a human eye with said spatially selective illumination and for reflecting infrared light in said spatially selective illumination towards a camera disposed along an optical axis such that an image obtained by said camera is superimposed of the illuminated eye and said infrared light reflected by said optical system;
    a controller for controlling illumination of said discrete pixels are and for controlling number of photons of said first wavelength per unit time per discrete pixel.

2. The system of claim 1 wherein said at least one light source includes a first laser for illuminating a first laser beam in said visible spectrum and a second laser for illuminating a second laser beam in said infrared spectrum, and wherein said system further a wavelength combiner for superimposing said first and second beams into said coherent beam.

3. The system of claim 2 wherein said wavelength combiner includes a first input fiber port for receiving said first beam and a second input fiber port for receiving said second beam, and an output fiber port for emitting said coherent beam, said wavelength combiner being configured such that said first and second wavelengths in said coherent beam are in the same spatial mode.

4. The system of claim 2 wherein said wavelength combiner includes beam splitter having a first input port for receiving said first beam and a second input port for receiving said second beam, and an output port for emitting said coherent beam, said beam splitter includes an optical alignment configured such that said first and second beams are spatially superimposed including said first and second wavelengths.

5. The system of claim 4 wherein said output port includes an optical fiber configured for propagation of said first and second wavelengths in said coherent beam are in the same spatial mode.

6. The system of claim 1 further comprising a stabilizing device for stabilizing the intensity of said visible light against fluctuations in the intensity of the visible light.

7. The system of claim 6 wherein said stabilizing device includes an acousto-optical crystal configured to receive and diffract light in said visible spectrum to any order other than the zero order.

8. The system of claim 6 further comprising feedback circuit having an output configured to drive said acousto-optical crystal by a harmonic signal in the radiofrequency spectrum, such that said intensity directly depends on amplitude of the harmonic signal.

9. The system of claim 6 further comprising a photodetector measuring the intensity of the visible light and wherein said feedback circuit includes an input formed as a difference of an output voltage of the photodetector and a reference voltage, said photodetector includes an optical filter configured for transmitting visible light and blocking infrared light such that intensity measured by the photodetector is only the intensity of the visible light.

10. The system of claim 9 wherein feedback circuit includes a voltage-controlled attenuator having an input of harmonic signal in the radiofrequency spectrum provided by a radiofrequency oscillator, said voltage-controlled attenuator being configured to provide an output signal having said frequency harmonic signal with an attenuated amplitude, wherein level of attenuation being controlled by a control voltage of said feedback circuit, and wherein said output signal is directed to a radiofrequency switch which drives a radiofrequency amplifier which drives the acousto-optical crystal.

11. The system of claim 10 wherein the radiofrequency switch cuts off the radiofrequency harmonic signal from said acousto-optic crystal and as a result modulates in time the intensity of the visible light, with the result that laser pulses can be formed with a time duration controlled by the voltage of the voltage-controlled radiofrequency switch.

12. The system of claim 11 further comprising a dichroic mirror configured to reflect majority of said visible light towards said photodetector and to transmit the entire infrared light, such that beam transmitted through the dichroic mirror contains visible and infrared light with intensities are at a ratio of 1:50.

13. The system of claim 1 wherein said LCD dot array includes LCD geometric arrangements disposed along said optical path and being configured such the laser beam passes therethrough.

14. The system of claim 13 wherein said optical path includes retroreflection prisms configured to allow passes of the laser beam through each one of said LCD geometric arrangements.

15. The system of claim 1 wherein said optical system includes a beam splitter with an antireflective coating for infrared light, in such a way that it is the laser beam exiting the beam splitter that propagates towards the eye, and in such a way that a viewing camera sensitive to infrared light and positioned behind the beam splitter and focusing on the eye's pupil can record the eye's pupil, without the image being blurred by infrared light virtual reflections from the beam splitter, as a result of the antireflective coating for infrared light.

16. The system of claim 15 further comprising a transparent glass positioned before the eye to be illuminated, in such a way that the infrared light of the laser beam is reflected backwards from the glass plate and is incident on the viewing camera after being transmitted though the beam splitter, in such a way that the viewing camera presents a superposition of the eye's pupil image with the arrangement of pixels of higher/lesser intensity, with the result that information can be registered on which particular points on the eye's pupil are being illuminated, with the further result that in subsequent measurements on the same human subject the same said spots can be systematically illuminated again.

17. The system of claim 16 further comprising a set of converging and diverging lenses disposed with respect to said beam splitter in such a way as to collimate the diverging light beams reflected from the cornea and direct them into the viewing camera.

* * * * *